US00PP33507P2

(12) United States Plant Patent
Meilland

(10) Patent No.: US PP33,507 P2
(45) Date of Patent: Sep. 28, 2021

(54) GROUND COVER ROSE PLANT NAMED 'MEIFRANJIN'

(50) Latin Name: *Rosa hybrida*
Varietal Denomination: MEIFRANJIN

(71) Applicant: THE CONARD PYLE COMPANY, West Grove, PA (US)

(72) Inventor: Alain Antoine Meilland, Antibes (FR)

(73) Assignee: THE CONARD PYLE COMPANY, West Grove, PA (US)

( * ) Notice: Subject to any disclaimer, the term of this patent is extended or adjusted under 35 U.S.C. 154(b) by 0 days.

(21) Appl. No.: 17/128,285

(22) Filed: Dec. 21, 2020

(51) Int. Cl.
*A01H 5/02* (2018.01)
*A01H 6/74* (2018.01)

(52) U.S. Cl.
USPC ..... Plt./101
CPC ..... *A01H 6/749* (2018.05)

(58) Field of Classification Search
USPC ..... Plt./101
CPC ..... A01H 6/749; A01H 5/02
See application file for complete search history.

(56) References Cited

U.S. PATENT DOCUMENTS

PP17,877 P3 7/2007 Meilland

*Primary Examiner* — Keith O. Robinson
(74) *Attorney, Agent, or Firm* — Panitch Schwarze Belisario & Nadel LLP; Stephany G. Small; Travis W. Bliss

(57) ABSTRACT

A new and distinct variety of ground cover rose plant, referred to by its cultivar name, 'MEIFRANJIN', is disclosed. The new variety forms on a nearly continuous basis attractive, cup shaped, pink double colored flowers. Attractive, dense and glossy foliage is formed, which contrasts beautifully with the blossoms. A ground cover growth habit is displayed. The new variety is well suited for providing attractive ornamentation in the landscape.

1 Drawing Sheet

Botanical/commercial classification:
Latin name: *Rosa hybrida.*
Varietal denomination: 'MEIFRANJIN'.

SUMMARY OF THE INVENTION

The new variety of *Rosa hybrida* plant was created by artificial pollination wherein two parents were crossed which previously had been studied in the hope that they would contribute the desired characteristics. The female parent (i.e., the seed parent) was the 'THE FAIRY' variety (non-patented). The male parent (i.e., the pollen parent) was an unnamed seedling (non-patented), which is the progeny of the cross between the 'KORMAX' variety (non-patented) and an unnamed seedling variety (non-patented).

The parentage of the new variety can be summarized as follows:

'THE FAIRY' x ('KORMAX' x Unnamed Seedling)

The seeds resulting from the above pollination were sown and small plants were obtained which were physically and biologically different from each other. Selective study resulted in the identification of a single plant of the new variety.

It was found that the new variety of rose plant of the present invention possesses the following combination of characteristics:

(a) forms a compact and well-balanced plant,
(b) provides pink colored double flower, and
(c) exhibits a dense and glossy foliage.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'THE FAIRY' variety (i.e., the seed parent) displays a more bushy growth habit compared to the new variety. The 'KORMAX' variety (i.e., the paternal grandmother) displays red colored flowers, whereas the new variety displays pink colored flowers. The unnamed seedling pollen parent from the cross ('KORMAX' x unnamed seedling) displays red with yellow eye colored flowers, whereas the new variety displays pink colored flowers. Moreover, the new variety can be readily distinguished from other similar non-parental varieties. For example, the 'MEIGALPIO' variety (U.S. Plant Pat. No. 17,877) displays red pink colored flowers, whereas the new variety displays pink colored flowers.

The new variety has been found to undergo asexual propagation in Le Cannet des Maures, Var, France by a number of routes, including softwood cuttings and grafting t-bud. Asexual propagation by the above-mentioned techniques in Le Cannet des Maures, Var, France has shown that the characteristics of the new variety are stable and are strictly transmissible by such asexual propagation from one generation to another. Accordingly, the new variety undergoes asexual propagation in a true-to-type manner.

The new variety has been named 'MEIFRANJIN'.

The new variety has not been offered for sale nor was the new variety publicly available at this time of filing the instant application.

BRIEF DESCRIPTION OF THE PHOTOGRAPH

The accompanying photograph of the drawing shows as nearly true as it is reasonably possible to make the same, in a color illustration of this character, typical specimens of the plant parts of the new variety. The rose plants of the new variety were approximately five (5) years of age and were observed during July while budded on their own roots and growing outdoors at Le Cannet des Maures, Var, France. Dimensions in centimeters are indicated at the bottom of the drawing.

Element 1—illustrates a specimen of a young shoot.

Element 2—illustrates a specimen of a floral bud before the opening of the sepals.

Element 3—illustrates a specimen of a floral bud at the opening of the sepals.

Element 4—illustrates a specimen of a floral bud at the opening of the petals.

Element 5—illustrates a specimen of a flower in the course of opening.

Element 6—illustrates a specimen of a fully open flower—plan view—observe.

Element 7—illustrates a specimen of a fully open flower—plan view—reverse.

Element 8—illustrates a specimen of an open flower—plan view—observe.

Element 9—illustrates a specimen of an open flower—plan view—reverse.

Element 10—illustrates a specimen of a floral receptacle showing arrangement of the stamens and pistils.

Element 11—illustrates a specimen of a floral receptacle showing arrangement of the pistils (stamens removed).

Element 12—illustrates a specimen of a flowering stem.

Element 13—illustrates a specimen of a leaf with 7 leaflets—plan view—upper surface.

Element 14—illustrates a specimen of a leaf with 7 leaflets—plan view—under surface.

Element 15—illustrates a specimen of blooms in a cluster.

DETAILED BOTANICAL DESCRIPTION

The chart used in the identification of the colors is that of The Royal Horticultural Society (R.H.S. Colour Chart, 2001 edition), London, England. The terminology which precedes reference to the chart has been added to indicate the corresponding color in more common terms. The description is based on the observation of five-years-old specimens of the new variety during July while budded on their own roots and growing outdoors at Le Cannet des Maures, Var, France.

Commercial classification: Ground Cover.

Plant:

*Habit*.—Ground cover.

*Height*.—Approximately 35 on average.

*Width*.—Approximately 50 average.

Branches:

*Color*.—Young stems: commonly near Yellow-Green Group 146B. — adult wood: commonly near Yellow-Green Group 146A.

*Length of main stem*.—Typically 30 to 50 cm on average.

*Young shoots*.—Anthocyanin coloration: medium intensity and commonly near Greyed-Red Group 178B.

*Thorns*.—Configuration on adult stems: elongated and curved downwards on the upper surface and concave on the under surface. — long prickles — quantity: commonly approximately 3 thorns per 10 cm long young stem and commonly 8 thorns per 10 cm long adult stem. — long prickles — base shape: oval. — long prickles — size: approximately 0.5 cm in length on average on young stems and approximately 0.8 cm in length on average on adult stems. — long prickles — color commonly near Greyed-Orange Group 164C on young stems and commonly near Greyed-Orange Group 166B on adult stems. — small prickles — quantity: absent.

Foliage:

*General appearance*.—Dense with a glossy aspect.

*Number of leaflets*.—3, 5, and 7; most often 7.

*Terminal leaflet*.—Length: approximately 3.5 cm on average. — width: approximately 3.0 cm on average.

*New foliage*.—Upper surface color: commonly near Yellow-Green Group 146B. — under surface color: commonly near Yellow-Green Group 147C. — anthocyanin coloration: commonly near Greyed-Red Group 178B.

*Adult foliage*.—Upper surface color: commonly near Green Group 137A. — under surface color: commonly near Yellow-Green Group 147B. — anthocyanin coloration: commonly near Greyed-Red Group 178B.

Leaflets:

*Shape*.—Tip: acuminate. — base: obtuse.

*Texture*.—Smooth.

*Glossiness of upper side*.—Strong.

*General appearance*.—Oval.

*Edge*.—Slightly denticulate.

*Serration*.—Small and single.

*Undulation on the margin*.—Weak to medium.

*Petiole rachis*.—Color of upper surface: commonly near Yellow-Green Group 144D. — color of under surface: commonly near Yellow-Green Group 144A.

*Petioles*.—Upper surface: no glandular. — under surface: few prickles. — color of upper surface: commonly near Yellow-Green Group 146A. — color of under surface: commonly near Yellow-Green Group 146C. — petiole length of terminal leaflet: approximately 2.2 cm on average.

*Stipules*.—General appearance: adnate, pectinate and narrow. — length: approximately 1.1 cm on average. — width: approximately 0.6 cm on average. — color of upper surface: commonly near between Yellow-Green Group 144D and Yellow-Green Group 144C. — color of under surface: commonly near Yellow- Green Group 144B.

Inflorescence:

*Number of flowers per stem*.—Typically 1 to 12 flowers per stem.

*Lastingness of the bloom*.—On the plant: approximately 12 to 15 days on average.

*Bud*.—Shape: conical. — size: small. — length: approximately 1.0 cm on average. — width: approximately 0.9 cm on average. — color as calyx breaks: upper surface: commonly between Red Group 51C and Red Group 51D, suffused with near Red Group 52D and very little spot at the base commonly near Yellow Group 2D. under surface: commonly between Red Group 51C and Red Group 51D, suffused with near Red Group 52D and very little spot at the base commonly near Yellow Group 2D.

*Sepals*.—Length: typically 1.0 to 1.2 cm on average. — width: approximately 0.6 cm on average. — shape: at the top: narrow and longish, at the base: upright. — extensions: absent. — upper surface:

texture: tomentous. color: commonly near Yellow-Green Group 148C. — under surface: texture: smooth. color commonly near Yellow-Green Group 144A.

*Receptacle*.—Color: commonly near Yellow-Green Group 144A. — length: approximately 0.5 cm on average. — width: approximately 0.4 cm on average. — surface: smooth. — shape: funnel shaped.

*Peduncle*.—Length: approximately 3.2 cm on average. — width: approximately 0.2 cm on average. — surface: smooth. — color: commonly near Yellow-Green Group 144A more or less suffused with near Greyed-Purple Group 178A.

*Flower*.—Average diameter when fully open: approximately 4.0 cm on average. — shape: cup shaped. — number of petals under normal conditions: typically 24 to 26 petals on average. — shape of the petal: base: obtuse. top: rounded. — petal margin: smooth. — texture of the petal: leathery. — petal length: typically 1.7 to 2.0 cm on average. — petal width: approximately 1.5 cm on average. — petal arrangement: imbricated without petaloids. — petal drop: petals drop off cleanly before drying. — fragrance: none. — color when opening: spot at the base: upper surface is commonly near Yellow Group 2D and under surface is commonly near Yellow Group 2D. upper surface of the flower: commonly near Red Group 52D suffused with near Red Group 52B. under surface of the flower: commonly near Red Group 52D suffused with near Red Group 52B. — color of the open flower: spot at the base: upper surface is commonly near Yellow Group 2D and under surface is commonly near Yellow Group 2D. upper surface of the flower: commonly near Red Group 52D. under surface of the flower: commonly near Red Group 52D. — anthers: number is approximately 59 on average, length is approximately 0.1 cm on average, coloration is commonly near Orange-Red Group 33C, and arrangement is regular around styles. — filaments: length is approximately 0.2 cm on average and coloration is commonly near Yellow Group 2C. — styles: length is approximately 0.2 cm on average, coloration is commonly near Yellow Group 2C, and number is approximately 31 on average. — stigmas: length is approximately 0.1 cm on average and coloration is commonly near Yellow Group 2C. — pollen: not available at this stage. — hips: not available at this stage.

Development:

*Vegetation*.—Strong.

*Blooming*.—Early in the season, very abundant and nearly continuous, typical from May to November in France.

*USDA hardiness zone*.—Zone 5.

*Tolerance to disease*.—Good, and particularly against black spot (*Diplocarpon rosae*) and rust (*Phragmidium* sp.).

The new 'MEIFRANJIN' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of rose plant named 'MEIFRANJIN' characterized by the following combination of characteristics:

(a) forms a compact and well-balanced plant, (b) provides pink colored double flower, and (c) exhibits a dense and glossy foliage;

substantially as herein shown and described.

* * * * *

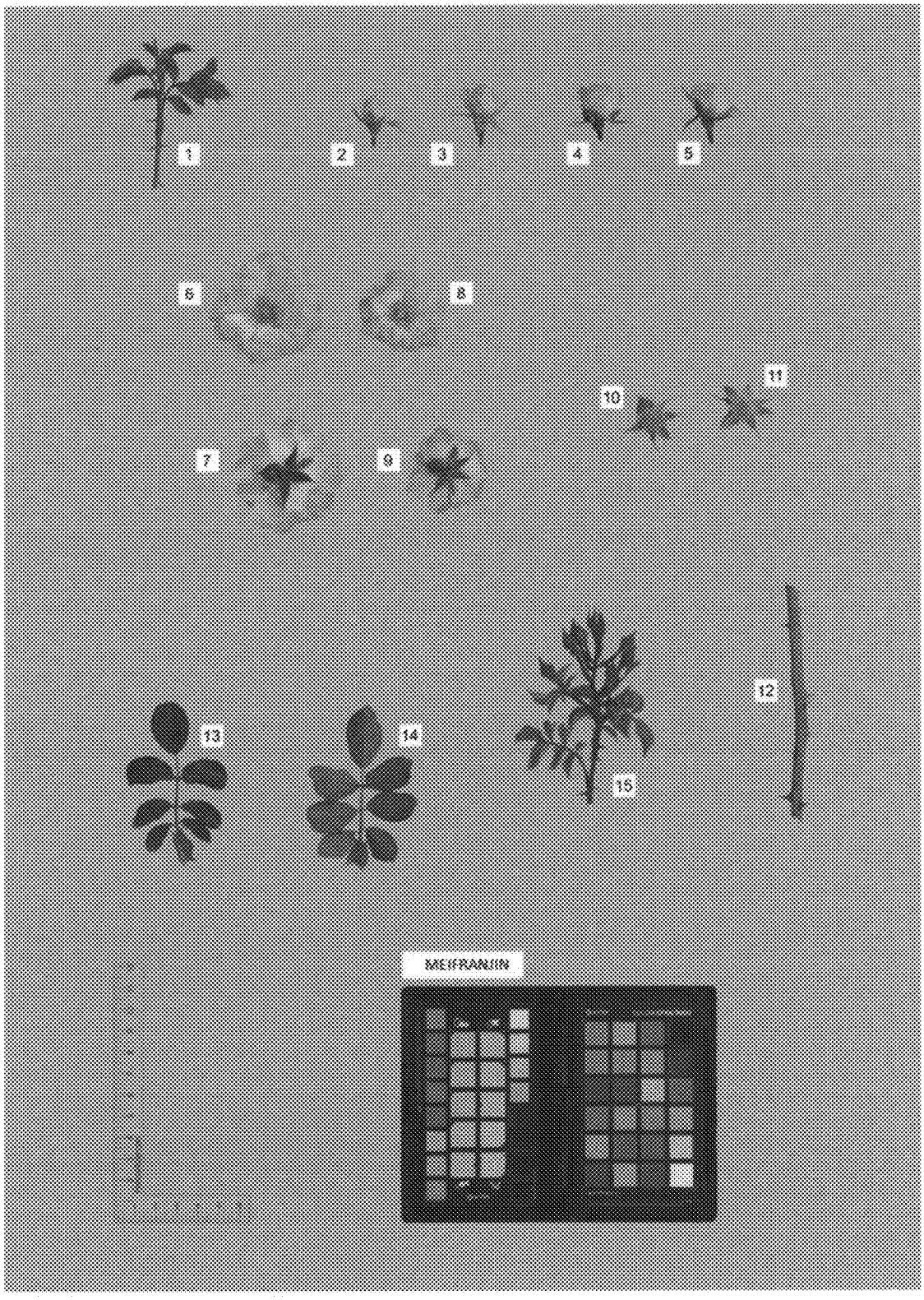
1
2
3
4
5
6
8
10
11
7
9
12
13
14
15
MEIFRANKIN